US008163519B2

(12) United States Patent
Ko et al.

(10) Patent No.: US 8,163,519 B2
(45) Date of Patent: Apr. 24, 2012

(54) FUNGAL IMMUNOMODULATORY PROTEIN (FIP) PREPARED BY MICROORGANISMS AND USES THEREOF

(76) Inventors: Jiunn-Liang Ko, Taipei (TW); Yu-Lu Huang, Taipei (TW); Tzu-Chih Chen, Taipei (TW); Hsu-Wei Hung, Taipei (TW); Ho-Lung Jiang, Taipei (TW); Ching-Lung Hu, Taipei (TW); Cheng-Chun Kuan, Taipei (TW); Hsuan-Ju Thou, Taipei (TW)

( * ) Notice: Subject to any disclaimer, the term of this patent is extended or adjusted under 35 U.S.C. 154(b) by 474 days.

(21) Appl. No.: 10/572,563

(22) PCT Filed: Sep. 14, 2004
(Under 37 CFR 1.47)

(86) PCT No.: PCT/CN2004/001044
§ 371 (c)(1),
(2), (4) Date: May 9, 2008

(87) PCT Pub. No.: WO2005/040375
PCT Pub. Date: May 6, 2005

(65) Prior Publication Data
US 2009/0042776 A1    Feb. 12, 2009

Related U.S. Application Data

(60) Provisional application No. 60/503,547, filed on Sep. 17, 2003.

(51) Int. Cl.
*C12P 21/04*    (2006.01)
*C12P 21/06*    (2006.01)
*A61K 39/00*    (2006.01)

(52) U.S. Cl. .................... 435/69.1; 435/71.1; 424/185.1

(58) Field of Classification Search ........................ None
See application file for complete search history.

(56) References Cited

U.S. PATENT DOCUMENTS

| 5,334,704 A | 8/1994 | Tsunoo et al. | 530/371 |
| 5,858,974 A * | 1/1999 | Little et al. | 514/12 |
| 5,928,896 A * | 7/1999 | Evans et al. | 435/69.1 |

FOREIGN PATENT DOCUMENTS

| JP | 02-032026 | 2/1990 |
| JP | 04-019423 | 1/1992 |
| JP | 06-283244 | 10/1994 |
| WO | WO 2004/092210 | 10/2004 |

OTHER PUBLICATIONS

Egel-Mitani et al (Gene vol. 73, pp. 113-120, 1988).*
Allione A, et al., β-*Galactoside-Binding Protein (βGBP) Alters the Cell Cycle, Up-Regulates Expression of the α- and β-Chains of the IFN-γ Receptor, and Triggers IFN-γ-Mediated Apoptosis of Activated Human T Lymphocytes*, J. Immunol. 161:2114-2119 (1998).
Black PH, *The Inflammatory Response is an Integral Part of the Stress Response: Implications for Atherosclerosis, Insulin Resistance, Type II Diabetes and Metabolic Syndrome X*, Brain Behav Immun. 17:350-364 (2003).
Boping YE, et al., *Prokaryotic Expressing of LZ-8 Gene in E-Coli*, Pharm. Biotechnol. 9:21-23 (2002).
Chen HY, et al., *In Vivo Anti-Candidal Activity Induced by a Traditional Chinese Herbal Medicine, Ganoderma lucidum*, Jpn. J. Med. Mycol. 33:505-512 (1992).
Couraud PO, et al., *Molecular Cloning, Characterization, and Expression of a Human 14-kDa Lectin*, J. Biol.Chem., 264:1310-1316 (1989).
Engelsma MY, et al., *Multiple Acute Temperature Stress Affects Leucoycte Populations and Antibody Responses in Common Carp, Cyprinus Carpio L.*, Fish Shellfish Immunol. 15:397-410 (2003).
Gabius HJ, et al., *The Immunomodulatory. γ-Galactoside-Specific Lectin from Mistletoe: Partial Sequence Analysis, Cell and Tissue Binding, and Impact on Intracellular Biosignalling of Monocytic Leukemia Cells*, Anticancer Res. 12:669-676 (1992).
Horner WE, et al., *Basidiomycete Allergens: Comparison of Three Ganoderma Species*, Allergy 48:110-116 (1993).
Jayaraman K, et al., *Polymerase Chain Reaction-Mediated Gene Synthesis: Synthesis of a Gene Coding for Isozyme C of Horseradish Peroxidase*, Proc. Natl. Acad. Sci. USA. 88:4084-4088 (1991).
Kawagishi H, et al., *5'Deoxy-5'-Methylsulphinyladenosine, A Platelet Aggregation Inhibitor from Ganoderma lucidum*, Phytochemistry 32:239-240 (1993).
Kino K, et al., *Isolation and Characterization of a New Immunomodulatory Protein, Ling Zhi-8 (LZ-8), from Ganoderma lucidium*, J. Biol. Chem. 264:472-478 (1989).
Ko JL, et al., *A New Fungal Immunomodulatory Protein, FIP-fve Isolated From the Edible Mushroom, Flammulina velutipes and Its Complete Amino Acid Sequence*, Eur. J. Biochem. 228:244-249 (1995). Laemmli, UK, et al., *Cleavage of Structural Proteins During the Assembly of the Head of Bacteriophage T4*, Nature 227:680-685 (1970).
Lin JM, et al., *Evaluation of the Anti-Inflammatory and Liver-Protective Effects of Anoectochilus formosanus, Ganoderma lucidum and Gynostemma pentaphyllum in Rats*, Am. J. Chin. Med. 21:59-69 (1993).
*Molecular Cloning*: A Laboratory Manual, $2^{nd}$ Ed., 1.82-1.84 (1989).
*Molecular Cloning*: A Laboratory Manual, $2^{nd}$ Ed., 18.60-18.75 (1989).
Murasugi A, et al., *Molecular Cloning of a cDNA and a Gene Encoding an Immunomodulatory Protein, Ling Zhi-8, from a Fungus, Ganoderma lucidum*, J. Biol. Chem. 266:2486-2493 (1991).

(Continued)

*Primary Examiner* — Albert Navarro
(74) *Attorney, Agent, or Firm* — Harness, Dickey & Pierce, P.L.C.

(57) ABSTRACT

The invention relates to an improved nucleic acid molecule encoding fungal immunomodulatory protein (FIP) that is better expressed in fungi, to vectors comprising the nucleic acid molecule, to hosts transformed with said vectors, to processes of expressing the protein of the invention in said transformed hosts, to the protein of the invention produced by said processes, to uses of said hosts comprising the protein of the invention and to a process of purifying FIP. The protein of the invention has wide immunomodulatory activity. Thus, the present invention further relates to uses of the protein of the invention in cosmetic or pharmaceutical compositions and to food or feed additives comprising the protein of the invention. Finally, the invention relates to the method of modulating immunological activities by orally administering FIP or proteins fused with FIP to a subject.

2 Claims, 16 Drawing Sheets

OTHER PUBLICATIONS

Romanos MA, et al., *Foreign Gene Expression in Yeast: a Review*, Yeast 8:423-488 (1992).

Sorensen MA, et al., *Absolute in Vivo Translation Rates of Individual Codons in Escherichia coli the Two Glutamic Acid Codons GAA and GAG are Translated with a Threefold Difference in Rate*, J. Mol. Biol. 222:265-280 (1991).

Saihong, Q, et al., *A Survey of Pharmacodynamic Study on Lucid Ganoderma*, Hunan Guiding Journal of TC MP 5:19-21 (1999).

Wasser SP, et al., *Therapeutic Effects of Substances Occurring in Higher Basidiomycetes Mushrooms: A Modern Perspective*, Crit. Rev. Immuno. 19:65-96 (1999).

Weisbart RH, et al., *Nuclear Delivery of p53 C-Terminal Peptides Into Cancer Cells Using scFv Fragments of a Monoclonal Antibody That Penetrates Living Cells*, Cancer Lett. 195:211-219 (2003).

PCT/CN2004/001044.

European Search Report dated Nov. 5, 2007 in corresponding European Application No. EP 04762178.4.

Tanaka, S., et al., "Complete Amino Acid Sequence of an Immunomodulatory Protein, Ling Zhi-8," J. Bio. Chem., vol. 264, No. 28, pp. 16372-16377 (Oct. 5, 1989).

van der Hem, L., et al., "Ling Zhi-8, Studies of a New Immunomodulating Agent," Transplantation, vol. 60, No. 5, pp. 438-443 (Sep. 16, 1995).

* cited by examiner

Figure 1

(I) DNA sequence of FIP-yeast :

```
ATGTCTGATA CTGCTTTGAT TTTCAGATTG GCTTGGGATG TTAAGAAGTT
GTCTTTCGAT TACACTCCAA ACTGGGGTAG AGGTAACCCA AACAACTTCA
TGATACTGTT ACTTTCCCAA AGGTTTTGAC TGATAAGGCT TACACTTACA
GAGTTGCTGT TTCTGGTAGA AACTTGGGTG TTAAGCCATC TTACGCTGTT
GAATCTGATG GTTCTCAAAA GGTTAACTTC TTGGAATACA ACTCTGGTTA
CGGTATTGCT GATACTAACA CTATTCAAGT TTTCGTTGTT GATCCAGATA
CTAACAACGA TTTCATTATT GCTCAATGGA ACTGA
```

(II) DNA sequence of FIP-lz :

```
ATGTCCGACA CTGCCTTGAT CTTCAGGCTC GCCTGGGACG TGAAGAAGCT
CTCGTTCGAC TACACCCCGA ACTGGGGCCG CGGCAACCCC AACAACTTCA
TCGACACTGT CACCTTCCCG AAAGTCTTGA CCGACAAGGC GTACACGTAC
CGCGTCGCCG TCTCCGGACG GAACCTCGGC GTGAAACCCT CGTACGCGGT
CGAGAGCGAC GGCTCGCAGA AGGTCAACTT CCTCGAGTAC AACTCCGGCT
ATGGCATAGC GGACACGAAC ACGATCCAGG TGTTCGTTGT CGACCCCGAC
ACCAACAACG ACTTCATCAT CGCCCAGTGG AACTAG
```

Figure 2

(I) Primer sequences of FIP-yeast (*Saccharomyces cerevisiae* codon):

i. forward primer

AAAAAAAAAA <u>GGATCCCGCA</u> ATGTCTGATA CTGCTTTGAT
          BamHI

ATGTCTGATA CTGCTTTGAT TTTCAGATTG GCTTGGGATG TTAAGAAGTT GTCTTTCGAT
AGGTAACCCA AACAACTTCA TTGATACTGT TACTTTCCCA AAGGTTTTGA CTGATAAGGC
TTTCTGGTAG AAACTTGGGT GTTAAGCCAT CTTACGCTGT TGAATCTGAT GGTTCTCAAA
AACTCTGGTT ACGGTATTGC TGATACTAAC ACTATTCAAG TTTTCGTTGT TGATCCAGAT ii. reverse primer AAAAAAAAAA A<u>CACGTGTCA</u> ACTAGTTAGT TCCATTGAGC A
          PmlI CTAGTTAGTT CCATTGAGCA ATAATGAAAT CGTTGTTAGT ATCTGGATCA ACAACGAAAA
GCAATACCGT AACCAGAGTT GTATTCCAAG AAGTTAACCT TTTGAGAACC ATCAGATTCA
ACCCAAGTTT CTACCAGAAA CAGCAACTCT GTAAGTGTAA GCCTTATCAG TCAAAACCTT
TGAAGTTGTT TGGGTTACCT CTACCCCAGT TGGAGTGTA ATCGAAAGAC AACTTCTTAA (II) Primer sequence of FIP-lz (*Ganoderma lucidum* codon):

i. forward primer

AAAAAAAAAA <u>GGATCCCGCA</u> ATGTCCGACA CTGCCTTGAT C
          BamHI

ATGTCCGACA CTGCCTTGAT TTCAGGCTCG CCTGGGACGT GAAGAAGCTC TCGTTCGACT
GGCAACCCCA CAACTTCAT CGACACTGTC ACCTTCCCGA AAGTCTTGAC CGACAAGGCG
CTCCGGACGG AACCTCGGCG TGAAACCCTC GTACGCGGTC GAGAGCGACG GCTCGCAGAA
ACTCCGGGTA TGGCATAGCG ACACGAACA CGATCCAGGT GTTCGTTGTC GACCCCGACA ii. reverse primer AAAAAAAAAA A<u>CACGTGTCA</u> ACTAGTTAGT TCCCTAGTTC CA
          PmlI CTAGTTAGTT CCCTAGTTCC ACTGGGCGAT GATGAAGTCG TTGTTGGTGT CGGGGTCGAC
ACGTGTCCGC TATGCCATAC CCGGAGTTGT ACTCGAGGAA GTTGACCTTC TGCGAGCCGT
CGTTTCACGC CGAGGTTCCG TCCGGAGACG GCGACGCGGT ACGTGTACGC CTTGTCGGTC
AGTGTCGATG AAGTTGTTGG GGTTGCCGCG GCCCCAGTTC GGGGTGTAGT CGAACGAGAG C

Figure 3

| | |
|---|---|
| Ganoderma lucidum | MSDTAL I FRL AWDVKKLSFD YTPNWGRGNP |
| Ganoderma tsugae | MSDTAL I FRL AWDVKKLSFD YTPNWGRGNP |
| Flamnulina velutips | SATSLT FQL A YLVKKIDFD YTPNWGRGTP |
| | |
| Ganoderma lucidum | NNFIDTVTFP KVLTDKAYTY RVAVSGRNLG |
| Ganoderma tsugae | NNFIDTVTFP KVLTDKAYTY RVAVSGRNLG |
| Flamnulina velutips | SSYIDNLTFP KVLTDKKYSY RVVVNGSDLG |
| | |
| Ganoderma lucidum | VKPSYAVESD GSQKVNFLEY NSGYG I ADTN |
| Ganoderma tsugae | VKPSYAVESD GSQKVNFLEY NSGYG I ADTN |
| Flamnulina velutips | VESNFAVTPS GGQTINFLQY NKGYG V ADTK |
| | |
| Ganoderma lucidum | TIQVFVVDPD TNNDF IIAQWN |
| Ganoderma tsugae | TIQVFVVDPD TNNDF IIAQWN |
| Flamnulina velutips | TIQVFVV PD TGNSEEYIIAEWKKT |

Figure 5
(I) pYB101-FIP-yeast
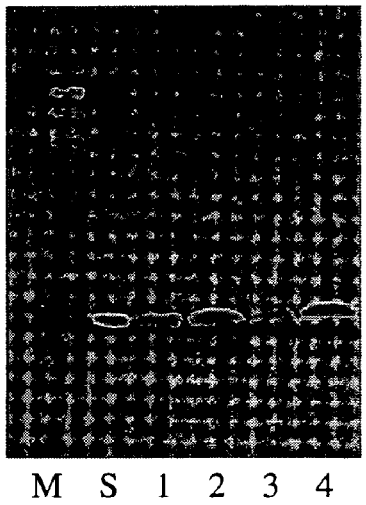
M  S  1  2  3  4
(II) pYB101-FIP-lz
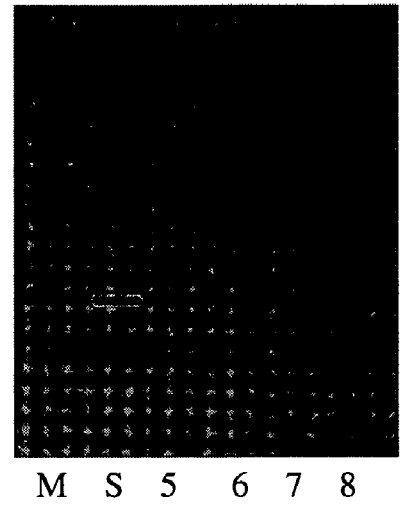
M  S  5  6  7  8

Figure 6

(I) forward primer

AAAAACTCGA GAAAAGAGAG GCTGAAGCTA TGTCCGACAC TGCCTTGAT
     XhoI (II) reverse primer AAAAACACGT GTCAACTAGT TAGTTCCATT G
     PmlI

Figure 7

α-factor leader sequence

|  |  |  |  |  |  |  | Met | Arg | Phe | Pro | Ser | Ile | Phe | Thr |
|---|---|---|---|---|---|---|---|---|---|---|---|---|---|---|
| CGG | TAC | CCG | G GG | ATC | CAA | ACG | ATG | AGA | TTT | CCT | TCA | ATT | TTT | ACT |
|  |  |  | *BamH*I |  |  |  |  |  |  |  |  |  |  |  |

| Ala | Val | Leu | Phe | Ala | Ala | Ser | Ser | Ala | Leu | Ala | Ala | Pro | Val | Asn |
|---|---|---|---|---|---|---|---|---|---|---|---|---|---|---|
| GCA | GTT | TTA | TTC | GCA | GCA | TCC | TCC | GCA | TTA | GCT | GCT | CCA | GTC | AAC |

| Thr | Thr | Thr | Glu | Asp | Glu | Thr | Ala | Gln | Ile | Pro | Ala | Glu | Ala | Val |
|---|---|---|---|---|---|---|---|---|---|---|---|---|---|---|
| ACT | ACA | ACA | GAA | GAT | GAA | ACG | GCA | CAA | ATT | CCG | GCT | GAA | GCT | GTC |

| Ile | Gly | Tyr | Ser | Asp | Leu | Glu | Gly | Asp | Phe | Asp | Val | Ala | Val | Leu |
|---|---|---|---|---|---|---|---|---|---|---|---|---|---|---|
| ATC | GGT | TAC | TCA | GAT | TTA | GAA | GGG | GAT | TTC | GAT | GTT | GCT | GTT | TTG |

| Pro | Phe | Ser | Asn | Ser | Thr | Asn | Asn | Gly | Leu | Leu | Phe | Ile | Asn | Thr |
|---|---|---|---|---|---|---|---|---|---|---|---|---|---|---|
| CCA | TTT | TCC | AAC | AGC | ACA | AAT | AAC | GGG | TTA | TTG | TTT | ATA | AAT | ACT |

| Thr | Ile | Ala | Ser | Ile | Ala | Ala | Lys | Glu | Glu | Gly | Val | Ser | Leu | Glu |
|---|---|---|---|---|---|---|---|---|---|---|---|---|---|---|
| ACT | ATT | GCC | AGC | ATT | GCT | GCT | AAA | GAA | GAA | GGG | GTA | TCT | CTC | GAG |
|  |  |  |  |  |  |  |  |  |  |  |  |  | *Xho*I |  |

Signal cleavage site

| Lys | Arg | Glu | Ala | Glu | Ala | Met | Ser | Asp | Thr | Ala | Leu | Ile | Phe | Arg |
|---|---|---|---|---|---|---|---|---|---|---|---|---|---|---|
| AAA | AGA | GAG | GCT | GAA | GCT | ATG | TCC | GAC | ACT | GCC | TTG | ATC | TTC | AGG |

FIP DNA sequence →

M  S  F

Figure 12
(I)
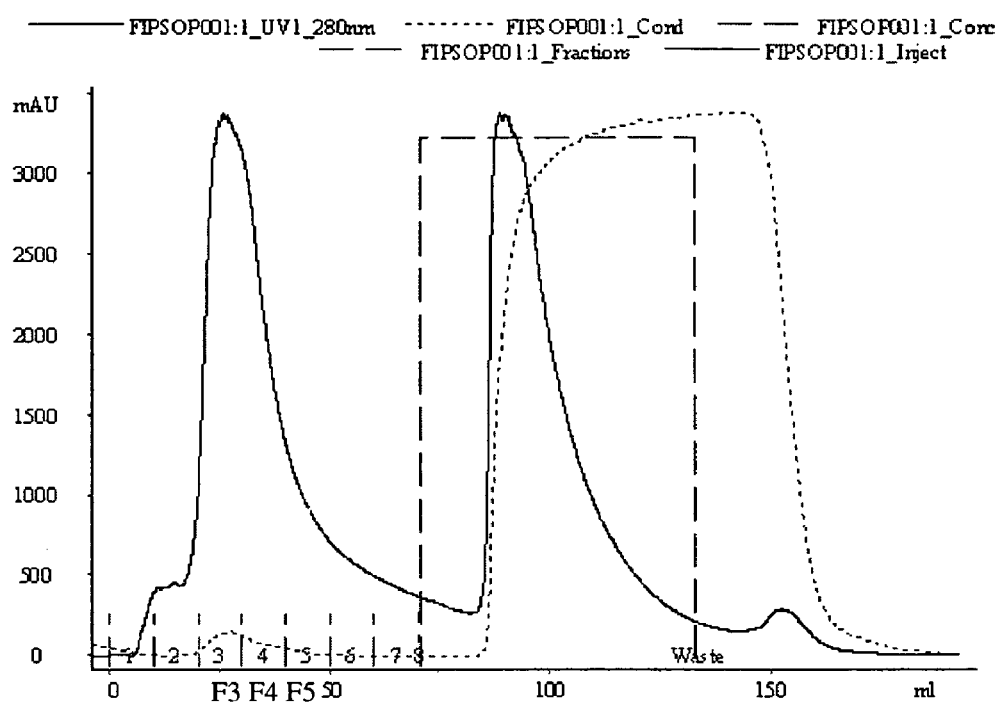
(II)
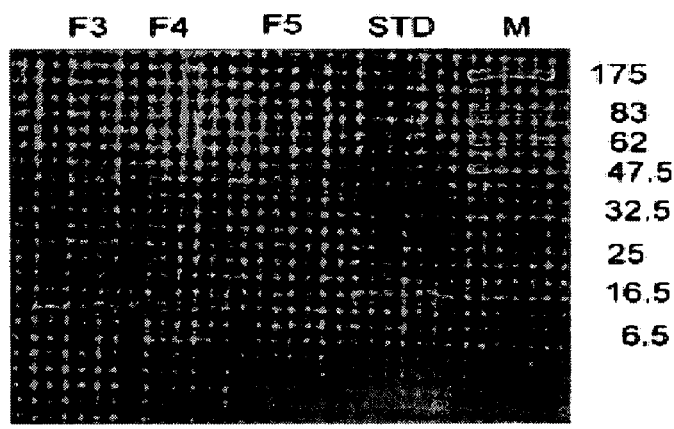

SEQUENCE LISTING

```
<160> NUMBER OF SEQ ID NOS: 15

<210> SEQ ID NO 1
<211> LENGTH: 336
<212> TYPE: DNA
<213> ORGANISM: Ganoderma lucidium
<220> FEATURE:
<221> NAME/KEY: variation
<222> LOCATION: (1)..(336)
<223> OTHER INFORMATION: improved DNA sequence of G. lucidium FIP for
      expressing in yeast, FIP-yeast

<400> SEQUENCE: 1
atgtctgata ctgctttgat tttcagattg gcttgggatg ttaagaagtt gtctttcgat      60
tacactccaa actggggtag aggtaaccca aacaacttca ttgatactgt tactttccca     120
aaggttttga ctgataaggc ttacacttac agagttgctg tttctggtag aaacttgggt     180
gttaagccat cttacgctgt tgaatctgat ggttctcaaa aggttaactt cttggaatac     240
aactctggtt acggtattgc tgatactaac actattcaag ttttcgttgt tgatccagat     300
actaacaacg atttcattat tgctcaatgg aactga                              336

<210> SEQ ID NO 2
<211> LENGTH: 336
<212> TYPE: DNA
<213> ORGANISM: Ganoderma lucidium
<220> FEATURE:
<221> NAME/KEY: gene
<222> LOCATION: (1)..(336)
<223> OTHER INFORMATION: original FIP codon, FIP-lz

<400> SEQUENCE: 2
atgtccgaca ctgccttgat cttcaggctc gcctgggacg tgaagaagct ctcgttcgac      60
tacaccccga actggggccg cggcaacccc aacaacttca tcgacactgt caccttcccg     120
aaagtcttga ccgacaaggc gtacacgtac cgcgtcgccg tctccggacg gaacctcggc     180
```

```
gtgaaaccct cgtacgcggt cgagagcgac ggctcgcaga aggtcaactt cctcgagtac    240
aactccgggt atggcatagc ggacacgaac acgatccagg tgttcgttgt cgaccccgac    300
accaacaacg acttcatcat cgcccagtgg aactag                              336
```

```
<210> SEQ ID NO 3
<211> LENGTH: 40
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(40)
<223> OTHER INFORMATION: forward primer of FIP-yeast

<400> SEQUENCE: 3
aaaaaaaaaa ggatcccgca atgtctgata ctgctttgat                          40

<210> SEQ ID NO 4
<211> LENGTH: 41
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(41)
<223> OTHER INFORMATION: reverse primer of FIP-yeast

<400> SEQUENCE: 4
aaaaaaaaaa acacgtgtca actagttagt tccattgagc a                        41

<210> SEQ ID NO 5
<211> LENGTH: 41
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(41)
<223> OTHER INFORMATION: forward primer of FIP-lz

<400> SEQUENCE: 5
aaaaaaaaaa ggatcccgca atgtccgaca ctgccttgat c                        41

<210> SEQ ID NO 6
<211> LENGTH: 42
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(42)
<223> OTHER INFORMATION: reverse primer of FIP-lz

<400> SEQUENCE: 6
aaaaaaaaaa acacgtgtca actagttagt tccctagttc ca                       42

<210> SEQ ID NO 7
<211> LENGTH: 111
<212> TYPE: PRT
<213> ORGANISM: Ganoderma lucidium
<220> FEATURE:
<221> NAME/KEY: PEPTIDE
<222> LOCATION: (1)..(111)
<223> OTHER INFORMATION: FIP amino acid sequence
```

```
<400> SEQUENCE: 7

Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
            20                  25                  30

Phe Ile Asp Thr Val Thr Phe Pro Lys Val Leu Thr Asp Lys Ala Tyr
        35                  40                  45

Thr Tyr Arg Val Ala Val Ser Gly Arg Asn Leu Gly Val Lys Pro Ser
    50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95

Val Asp Pro Asp Thr Asn Asn Asp Phe Ile Ile Ala Gln Trp Asn
                100                 105                 110

<210> SEQ ID NO 8
<211> LENGTH: 111
<212> TYPE: PRT
<213> ORGANISM: Ganoderma tsugae
<220> FEATURE:
<221> NAME/KEY: PEPTIDE
<222> LOCATION: (1)..(111)
<223> OTHER INFORMATION: FIP amino acid sequence

<400> SEQUENCE: 8

Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
            20                  25                  30

Phe Ile Asp Thr Val Thr Phe Pro Lys Val Leu Thr Asp Lys Ala Tyr
        35                  40                  45

Thr Tyr Arg Val Ala Val Ser Gly Arg Asn Leu Gly Val Lys Pro Ser
    50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95

Val Asp Pro Asp Thr Asn Asn Asp Phe Ile Ile Ala Gln Trp Asn
                100                 105                 110

<210> SEQ ID NO 9
<211> LENGTH: 113
<212> TYPE: PRT
<213> ORGANISM: Flamnulina velutips
<220> FEATURE:
<221> NAME/KEY: PEPTIDE
<222> LOCATION: (1)..(113)
<223> OTHER INFORMATION: FIP amino acid sequence

<400> SEQUENCE: 9

Ser Ala Thr Ser Leu Thr Phe Gln Leu Ala Tyr Leu Val Lys Lys Ile
1               5                   10                  15

Asp Phe Asp Tyr Thr Pro Asn Trp Gly Arg Gly Thr Pro Ser Ser Tyr
            20                  25                  30

Ile Asp Asn Leu Thr Phe Pro Lys Val Leu Thr Asp Lys Lys Tyr Ser
        35                  40                  45

Tyr Arg Val Val Val Asn Gly Ser Asp Leu Gly Val Glu Ser Asn Phe
    50                  55                  60
```

```
Ala Val Thr Pro Ser Gly Gly Gln Thr Ile Asn Phe Leu Gln Tyr Asn
 65                  70                  75                  80

Lys Gly Tyr Gly Val Ala Asp Thr Lys Thr Ile Gln Val Phe Val Val
                 85                  90                  95

Pro Asp Thr Gly Asn Ser Glu Glu Tyr Ile Ile Ala Glu Trp Lys Lys
            100                 105                 110

Thr

<210> SEQ ID NO 10
<211> LENGTH: 49
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(49)
<223> OTHER INFORMATION: forward primer of FIP

<400> SEQUENCE: 10
aaaaactcga gaaagagag gctgaagcta tgtccgacac tgccttgat              49

<210> SEQ ID NO 11
<211> LENGTH: 31
<212> TYPE: DNA
<213> ORGANISM: Artificial
<220> FEATURE:
<223> OTHER INFORMATION: primer
<220> FEATURE:
<221> NAME/KEY: primer
<222> LOCATION: (1)..(31)
<223> OTHER INFORMATION: reverse primer of FIP

<400> SEQUENCE: 11
aaaaacacgt gtcaactagt tagttccatt g                                31

<210> SEQ ID NO 12
<211> LENGTH: 315
<212> TYPE: DNA
<213> ORGANISM: Artificial
<220> FEATURE:
<223> OTHER INFORMATION: recombinant DNA sequence for encoding
      recombinant protein
<220> FEATURE:
<221> NAME/KEY: CDS
<222> LOCATION: (22)..(315)
<223> OTHER INFORMATION: recombinant protein containing alpha-factor and
      partial FIP

<400> SEQUENCE: 12
cggtacccgg ggatccaaac g atg aga ttt cct tca att ttt act gca gtt    51
                       Met Arg Phe Pro Ser Ile Phe Thr Ala Val
                        1               5                  10 tta ttc gca gca tcc tcc gca tta gct gct cca gtc aac act aca aca    99
Leu Phe Ala Ala Ser Ser Ala Leu Ala Ala Pro Val Asn Thr Thr Thr
            15                  20                  25 gaa gat gaa acg gca caa att ccg gct gaa gct gtc atc ggt tac tca   147
Glu Asp Glu Thr Ala Gln Ile Pro Ala Glu Ala Val Ile Gly Tyr Ser
        30                  35                  40 gat tta gaa ggg gat ttc gat gtt gct gtt ttg cca ttt tcc aac agc   195
Asp Leu Glu Gly Asp Phe Asp Val Ala Val Leu Pro Phe Ser Asn Ser
    45                  50                  55 aca aat aac ggg tta ttg ttt ata aat act act att gcc agc att gct   243
Thr Asn Asn Gly Leu Leu Phe Ile Asn Thr Thr Ile Ala Ser Ile Ala
 60                  65                  70
```

```
gct aaa gaa gaa ggg gta tct ctc gag aaa aga gag gct gaa gct atg      291
Ala Lys Glu Glu Gly Val Ser Leu Glu Lys Arg Glu Ala Glu Ala Met
 75              80                  85                  90 tcc gac act gcc ttg atc ttc agg                                      315
Ser Asp Thr Ala Leu Ile Phe Arg
                 95
```

<210> SEQ ID NO 13
<211> LENGTH: 98
<212> TYPE: PRT
<213> ORGANISM: Artificial
<220> FEATURE:
<223> OTHER INFORMATION: Synthetic Construct

<400> SEQUENCE: 13

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala Met Ser Asp Thr Ala Leu Ile
             85                  90                  95

Phe Arg
```

<210> SEQ ID NO 14
<211> LENGTH: 624
<212> TYPE: DNA
<213> ORGANISM: Artificial
<220> FEATURE:
<223> OTHER INFORMATION: recombinant sequence
<220> FEATURE:
<221> NAME/KEY: CDS
<222> LOCATION: (22)..(624)
<223> OTHER INFORMATION: recombinant sequence comprising alpha-factor
      and FIP

<400> SEQUENCE: 14

```
cggtacccgg ggatccaaac g atg aga ttt cct tca att ttt act gca gtt    51
                       Met Arg Phe Pro Ser Ile Phe Thr Ala Val
                        1               5                  10 tta ttc gca gca tcc tcc gca tta gct gct cca gtc aac act aca aca     99
Leu Phe Ala Ala Ser Ser Ala Leu Ala Ala Pro Val Asn Thr Thr Thr
             15                  20                  25 gaa gat gaa acg gca caa att ccg gct gaa gct gtc atc ggt tac tca    147
Glu Asp Glu Thr Ala Gln Ile Pro Ala Glu Ala Val Ile Gly Tyr Ser
         30                  35                  40 gat tta gaa ggg gat ttc gat gtt gct gtt ttg cca ttt tcc aac agc    195
Asp Leu Glu Gly Asp Phe Asp Val Ala Val Leu Pro Phe Ser Asn Ser
     45                  50                  55 aca aat aac ggg tta ttg ttt ata aat act act att gcc agc att gct    243
Thr Asn Asn Gly Leu Leu Phe Ile Asn Thr Thr Ile Ala Ser Ile Ala
 60                  65                  70 gct aaa gaa gaa ggg gta tct ctc gag aaa aga gag gct gaa gct atg    291
Ala Lys Glu Glu Gly Val Ser Leu Glu Lys Arg Glu Ala Glu Ala Met
 75              80                  85                  90
```

```
tct gat act gct ttg att ttc aga ttg gct tgg gat gtt aag aag ttg      339
Ser Asp Thr Ala Leu Ile Phe Arg Leu Ala Trp Asp Val Lys Lys Leu
            95                  100                 105 tct ttc gat tac act cca aac tgg ggt aga ggt aac cca aac aac ttc      387
Ser Phe Asp Tyr Thr Pro Asn Trp Gly Arg Gly Asn Pro Asn Asn Phe
        110                 115                 120 att gat act gtt act ttc cca aag gtt ttg act gat aag gct tac act      435
Ile Asp Thr Val Thr Phe Pro Lys Val Leu Thr Asp Lys Ala Tyr Thr
            125                 130                 135 tac aga gtt gct gtt tct ggt aga aac ttg ggt gtt aag cca tct tac      483
Tyr Arg Val Ala Val Ser Gly Arg Asn Leu Gly Val Lys Pro Ser Tyr
        140                 145                 150 gct gtt gaa tct gat ggt tct caa aag gtt aac ttc ttg gaa tac aac      531
Ala Val Glu Ser Asp Gly Ser Gln Lys Val Asn Phe Leu Glu Tyr Asn
155                 160                 165                 170 tct ggt tac ggt att gct gat act aac act att caa gtt ttc gtt gtt      579
Ser Gly Tyr Gly Ile Ala Asp Thr Asn Thr Ile Gln Val Phe Val Val
                175                 180                 185 gat cca gat act aac aac gat ttc att att gct caa tgg aac tga          624
Asp Pro Asp Thr Asn Asn Asp Phe Ile Ile Ala Gln Trp Asn
            190                 195                 200

<210> SEQ ID NO 15
<211> LENGTH: 200
<212> TYPE: PRT
<213> ORGANISM: Artificial
<220> FEATURE:
<223> OTHER INFORMATION: Synthetic Construct

<400> SEQUENCE: 15

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Met Ser Asp Thr Ala Leu Ile
                85                  90                  95

Phe Arg Leu Ala Trp Asp Val Lys Lys Leu Ser Phe Asp Tyr Thr Pro
            100                 105                 110

Asn Trp Gly Arg Gly Asn Pro Asn Asn Phe Ile Asp Thr Val Thr Phe
        115                 120                 125

Pro Lys Val Leu Thr Asp Lys Ala Tyr Thr Tyr Arg Val Ala Val Ser
    130                 135                 140

Gly Arg Asn Leu Gly Val Lys Pro Ser Tyr Ala Val Glu Ser Asp Gly
145                 150                 155                 160

Ser Gln Lys Val Asn Phe Leu Glu Tyr Asn Ser Gly Tyr Gly Ile Ala
                165                 170                 175

Asp Thr Asn Thr Ile Gln Val Phe Val Val Asp Pro Asp Thr Asn Asn
            180                 185                 190

Asp Phe Ile Ile Ala Gln Trp Asn
        195                 200
```

FUNGAL IMMUNOMODULATORY PROTEIN (FIP) PREPARED BY MICROORGANISMS AND USES THEREOF

CROSS-REFERENCE TO RELATED APPLICATIONS

This application is a National Stage entry of PCT Patent Application No. PCT/CN2004/001044, filed Sep. 14, 2004, which claims priority under 35 U.S.C. §§119(e), 120 and 365(c) to U.S. Provisional Application No. 60/503,547, filed Sep. 17, 2003, respectively.

BACKGROUND OF THE INVENTION

1. Field of the Invention

The invention relates to an improved nucleic acid molecule encoding fungal immunomodulatory protein (FIP) that is better expressed in fungi, to vectors comprising the nucleic acid molecule, to hosts transformed with said vectors, to processes of expressing the protein of the invention in said transformed hosts, to the protein of the invention produced by said processes, to uses of said hosts comprising the protein of the invention and to a process of purifying FIP. The protein of the invention has wide immunomodulatory activity. Thus, the present invention further relates to uses of the protein of the invention in cosmetic or pharmaceutical compositions and to food or feed additives comprising the protein of the invention. Finally, the invention relates to the method of modulating immunological activities by orally administering FIP or proteins fused with FIP to a subject.

2. Description of the Prior Art

Lectins from Fungal fruit bodies or mycelia have immunomodulatory and hepatoprotective effects that have been suggested to be able to remove free radicals (Lin J. M. et al., *Am J Chin Med.* 1993; 21(1):59-69). (L)-galactoside-specific lectins from mistletoe enhance cytokine production in vitro and in vivo (Gabius H. J. et al., *Anticancer Res.* 1992 May-June; 12(3):669-75). In a test using Balb/C mouse as the disease model, lectins and recombinant lectins can inhibit tumor formation (Couraud P. O. et al., *J. Biol. Chem.* 1989; 264:1310-1316).

*Ganoderma* is a rare and valuable herb in Chinese medicine. It has been known in China for over 5,000 years as "Ling Zhi". There are a variety of ganodenmas, including *G. lucidum* (red), *G. applanatum* (brown), *G. tsugae* (red), *G. sinense* (black), and *G. oregonense* (dark brown).

Several proteins from edible fungi such as *Ganoderma Lucidium* (Ling zhi or Reishi), *Volvariella Volvacea* (Chinese Mushroom), *Flammulina Velutipes* (Golden needle mushroom) share similar amino acid sequences and immunomodulatory functions. These proteins were named fungal immunomodulatory proteins (FIPs) (Ko J. L., *Eur. J. Biochem.* 1995; 228:224-249). Among all health foods in Chinese medicine, Ling Zhi is the best-studied fungus.

It has been known that Ling Zhi has anti-allergy (Chen H. Y et al., *J. Med. Mycol.* 1992; 33:505-512), hepatoprotective (Lin J. M. et al., *Am J Chin Med.* 1993; 21(1):59-69), anti-tumor effects (Wasser S P (1999), *Crit. Rev Immunol* 19:65-96) and immune advantages (Kino (1989), *Journal of Biological Chemistry* 264(1): 472-8). However, Ling Zhi is used restrictedly in the form of extract of raw material (Horner W. E. et al., *Allergy* 1993; 48:110-116) or small molecules (Kawagishi H., et al., *Phytochemistry* 1993; 32: 239-241).

One FIP purified from Ling Zhi, LZ-8 (Ling Zhi-8), has positive effects on systemic anaphylaxis (Kino K. et al., *J. Biol. Chem.* 1989; January 5; 264(1):472-8). LZ-8 has been used for the treatment of liver cancer and to prevent diabetes (Kino K. et al., *J. Biol. Chem.* 1989; January 5; 264(1):472-8). LZ-8 and another immunomodulatory protein FIP-five obtained from *Flammulina Velutipes* have similar amino acid sequences and folding structures similar to the heavy chain of immunoglobulin. Further, it has been shown that by enhancing the expression of LZ-8, these proteins show immunomodulatory activities and have positive effects on patients with systemic anaphylaxis (Ko J. L., *Eur. J. Biochem.* 1995; 228:224-249).

Baker's yeast is a safe microorganism widely used in traditional food processing (such as bread, wine). Baker's yeast is the typical model organism to study genetics, physiology and molecular biology. Because of its safety, baker's yeast was also successfully utilized to produce protein drugs such as Hirudin, Hemoglobulin, Urokinase, HSA (human serum albumin), IGF-I (insulin-like growth factor 1), GM-CSF (granulocyte macrophage colony stimulating factor), hepatitis B vaccine, etc. (Romanos M. A. et al., Yeast 1992; 8: 423-488). The proper host yeast used to produce the designate protein was selected according to the expression profile of the protein expressed. For example, *Saccharomyces cerevisiae* could be used in the production of food and protein drugs.

At the current stage, LZ-8 can only be obtained from Ling Zhi by a complicated and time-exhausting preparation protocol (such as extraction, U.S. Pat. No. 5,334,704). Although there is a great demand of Ling Zhi, natural Ling Zhi is rare and only grows on aged trees in steep mountains. Therefore, a technique to provide constant supply of high quality *Ganoderma* is needed. Currently there is no protocol for massive production of LZ-8 available.

Using the protocol described in the previous study (U.S. Pat. No. 5,334,704), the production of Ling Zhi immunomodulatory protein by extraction and purification is in lower efficiency and requires a higher cost. Other methods using *E. coli* to produce Ling Zhi immunomodulatory protein may have endotoxin contamination and the process of purification still requires a higher cost. Methods using mammalian cells to produce Ling Zhi immunomodulatory proteins require expensive medium and may meet viral or prion contamination.

U.S. Pat. No. 5,334,704 has disclosed that the glycoprotein isolated from *ganoderma* have immunosuppressive activity. The preparation of the glycoprotein includes steps of culturing *ganoderma* mycelia, extracting the resultant mycelia with an aqueous solvent and purifying the target protein from the resultant extract. The technique of the patent, which requires growing fungi and purifying the target protein from the fungi, requires a higher cost and is much more complicated than growing microorganism in vitro and is difficult to conduct industrial application.

SUMMARY OF THE INVENTION

The present invention provides an isolated nucleic acid molecule comprising a nucleic acid sequence as depicted in FIG. 1(I).

The present invention also provides vectors and host cells transformed with vectors.

The present invention further provides a process for preparing a host cell comprising FIP.

The present invention further provides the FIP prepared by said processes.

The present invention further provides uses of said host cells comprising FIP.

The present invention further provides processes of purifying FIP from said host transformed with said vectors.

The present invention further provides a composition comprising the FIP of the invention. The composition can be applied to cosmetics, pharmaceuticals, foods and feed additives.

The present invention further provides a method of orally administering FIP or protein fused with FIP to a subject to modulate its immunological activity.

BRIEF DESCRIPTION OF THE DRAWINGS

FIG. 1 shows the nucleotide sequence of the (I) improved FIP codon expressed by *Saccharomyces cerevisiae*, FIP-yeast; (II) the original FIP codon expressed by *Ganoderma lucidium*, FIP-1z.

FIG. 2 shows the nucleotide sequences and restriction sites of (I) the forward and reverse primers of the improved codons of *Saccharomyces cerevisiae*, the FIP-yeast; (II) the forward and reverse primers of the original codons of *Ganoderma lucidium*, the FIP-1z.

FIG. 3 shows the comparison of FIP amino acid sequences expressed in *Ganoderma lucidium*, *Ganoderma tsugae* and *Flamnulina velutips*. Identical amino acids are indicated in bold.

FIG. 5 shows the quantification of FIP expressed by yeast (DY150 or by4741) transformed with (I) pYB101-FIP-yeast or (II) pYB101-FIP-1z. M: Standard protein showing molecular mass 175, 83, 62, 47.5, 32.5, 25, 16.5, and 6.5 Kd. S: The standard FIP prepared from transformed *E. Coli*. Lane 1-2: Dy150 yeast No. 1-2 transformed with pYB101-FIP-yeast. Lane 3-4: By4741 yeast No. 1-2 transformed with pYB101-FIP-yeast. Lane 5-6: By4741 yeast No. 1-2 transformed with pYB101-FIP-1z. Lane 7-8: Dy150 yeast No. 1-2 transformed with pYB101-FIP-1z.

FIG. 6 shows the nucleotide sequences and restriction sites of (I) the forward and (II) reverse primers of the FIP.

FIG. 7 shows the nucleotide sequence and restriction sites of the –factor leader sequence used to generate pYB101s and pYB101s-FIP. The restriction sites are marked in bold. The beginning of the –factor leader sequence and the FIP gene is marked with an arrow.

FIG. 12 depicts the analysis of protein fractions using ÄKTA™ explorer 10S system. F3, F4 and F5 are the 3$^{rd}$, 4$^{th}$, and 5$^{th}$ sample tubes collected. (II) SDS-PAGE of the purified FIP fractions collected by ÄKTA™ explorer 10S system. M: Standard proteins showing molecular mass 175, 83, 62, 47.5, 32.5, 25, 16.5, and 6.5 Kd. STD: The standard FIP prepared from transformed *E. Coli*.

DETAILED DESCRIPTION OF THE INVENTION

Since Baker's yeast and Ling Zhi both belong to the fungi kingdom; yeast is expected to perform similar protein modifications (such as glycosylation and disulfide-bond formation) as Ling Zhi when expressing heterologous proteins from Ling Zhi.

The present invention provides an isolated nucleic acid molecule comprising a nucleic acid sequence as follows:

```
                                            (SEQ. ID NO. 1)
ATGTCTGATA CTGCTTTGAT TTTCAGATTG GCTTGGGATG

TTAAGAAGTT GTCTTTCGAT TACACTCCAA ACTGGGGTAG

AGGTAACCCA AACAACTTCA TTGATACTGT TACTTTCCCA

AAGGTTTTGA CTGATAAGGC TTACACTTAC AGAGTTGCTG

TTTCTGGTAG AAACTTGGGT GTTAAGCCAT CTTACGCTGT

TGAATCTGAT GGTTCTCAAA AGGTTAACTT CTTGGAATAC

AACTCTGGTT ACGGTATTGC TGATACTAAC ACTATTCAAG

TTTTCGTTGT TGATCCAGAT ACTAACAACG ATTTCATTAT

TGCTCAATGG AACTGA.
```

The present invention further provides the said nuclei acid molecule ligated to an additional signal sequence for secretion. Accordingly, the FIP expressed by host cells, which were transformed with the novel ligation nuclei acid molecule, would be directly secreted into the extracellular fluid and be easily separated from host cells at a lower cost.

The present invention further provides a ligation gene that can be generated by ligating the said nuclei acid molecule with other genes. Fusion protein composed of different proteins has been generated to provide additive bio-function of both composite proteins (Weisbart R H, *Cancer Lett*. 2003; 195(2):211-9.). Since FIP can be absorbed in the digestion system, by fusing FIP with other proteins, FIP can be used as a delivery system to carry other proteins into the target organism. And orally administering the fusion protein should supply benefits of both genes composite of the fusion gene to the target organism.

The present invention further provides a vector comprising the said nucleic acid molecule. The vector can be transformed into host cells. The vector may be circular or integrated plasmid depending on different uses and conditions.

The present invention further provides a host cell that is transformed with the vector said. The host cell may be a bacterium, a fungal cell or a yeast cell. The host cell said may be in intact or disrupted form.

The preferred embodiments of the host cell said are *Saccharomyces cerevisiae, Pichia pastoris, Hansenula polymorpha, Candida utilis, Candida boidinii, Candida maltosa, Kluyveromyces lactis, Yarrowia lipolytica, Schwanniomyces occidentalis, Schizosaccaromyces pombe, Torulopsis, Arxula adeninivorans*, or *Aspergillus (A. nidulans, A. niger, A. awamori, A. oryzae), Tricoderma (T. reesei)*. Cells from plants are also the preferred embodiment of the host cell.

Figure 4:
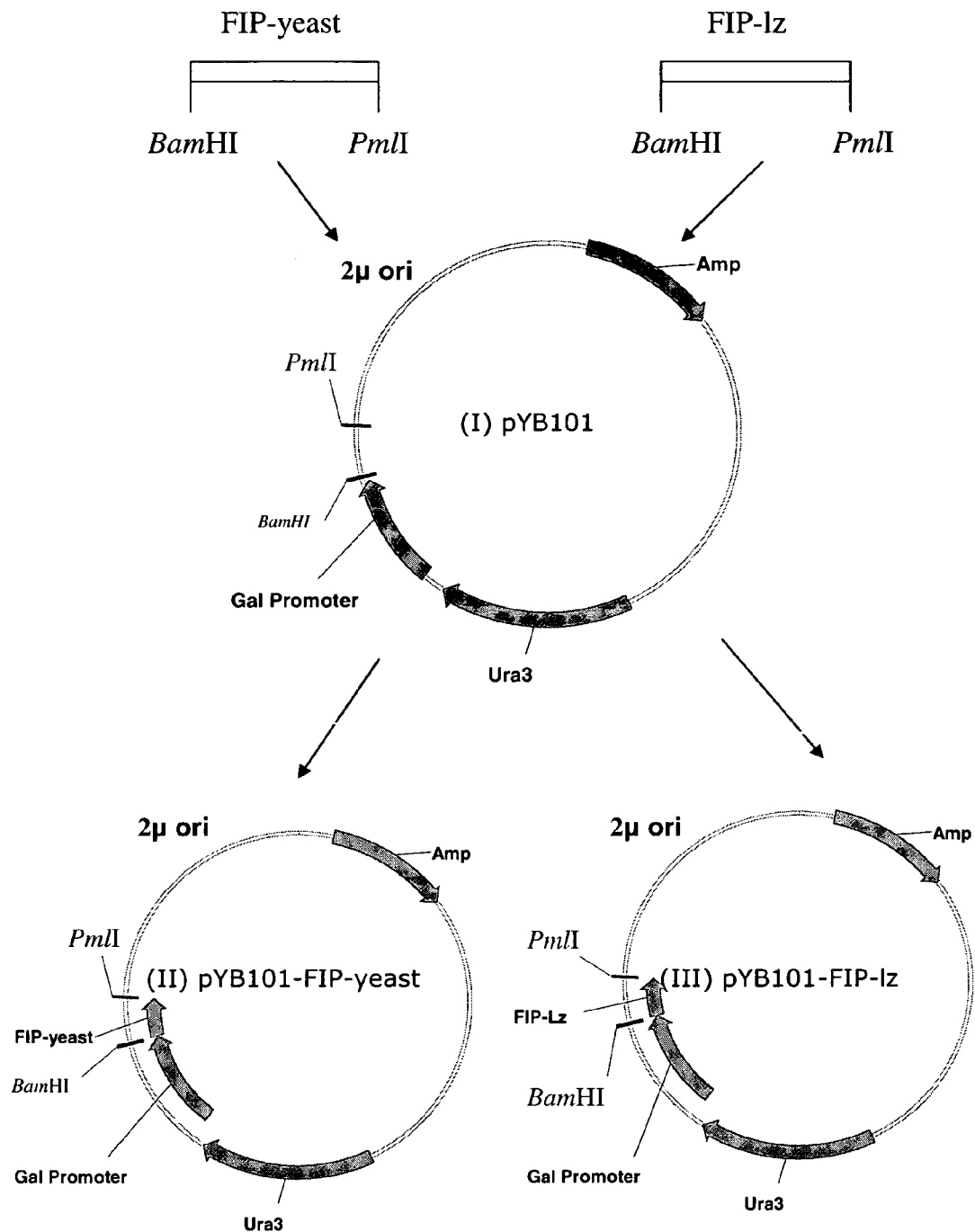
FIG. 4 illustrates the construct map of plasmid (I) pYB101 (II) pYB101-FIP-yeast (III) pYB101-FIP-1z.

The present invention also provides a process for preparing a host cell with FIP. The process comprises (a) constructing an expression vector having the improved FIP nucleotide sequence inserted, (b) transforming a host cell with the vector; and (c) culturing the transformed host cell under appropriate conditions. The preferred embodiment of the protein of the invention is depicted in FIG. 3. The preferred embodiments of the host cell said are *Saccharomyces cerevisiae, Pichia pastoris, Hansenula polymorpha, Candida utilis, Candida boidinii, Candida maltosa, Kluyveromyces lactis, Yarrowia lipolytica, Schwanniomyces occidentalis, Schizosaccaromyces pombe, Torulopsis, Arxula adeninivorans*, or *Aspergillus (A. nidulans, A. niger, A. awamori, A. oryzae), Tricoderma (T. reesei)*. Cells from plants are also the preferred embodiment of the host cell. The most preferred embodiment of host cell in step (b and c) is *Saccharomyces cerevisiae*. The vectors in step (b) are pYB101-FIP-yeast or pYB101-FIP-1z as depicted in FIG. 4(II,III). The FIP codon that was better expressed in fungi (FIG. 1(I)) was chosen based on its high tRNA translation efficiency (Sorensen M A, Pedersen S. *J Mol. Biol.* 1991; 222(2):265-80).

The present invention further provides uses of host cells comprising the FIP. For example, intact yeasts comprising the FIP can be orally administered to and absorbed by the target organism without purifying the protein from the host, thereby reducing the cost of utilization.

The present invention further provides a process of purifying FIP from the said host cells transformed with the said vector, the process comprising (a) dissolving fermented host cells in a solvent; (b) disrupting cells, (c) modify the pH of the solution to pH 4-5; (d) separating debris in the cell extracts; (e) centrifuging the supernatant; (f) adding the supernatant to the column equilibrated to pH 4-5; and (g) eluting the Ling Zhi immunomodulatory protein. In particular, the purification process comprising steps of (a) dissolving fermented yeasts 1:5-1:20 (v/v) in 5-50 mM PBS (Sigma); (b) disrupting cells in the cell extracts by the disruptor, (c) modify the pH of the solution to pH 4-5; (d) separating debris by centrifuging the solution at 3000 g for 15 minutes; (e) centrifuging the supernatant again at 12,000 g for 1 minute; (f) adding the supernatant to the CM Sepharose column (Amersham Biosciences) equilibrated to pH 4-5; and (g) eluting the Ling Zhi immunomodulatory protein by adding 20-50 mM acetic acid at pH 4-5.

The present invention also provides the protein of the invention that is prepared by the said process.

The present invention also relates to the route by which FIP or the host cell comprising FIP is administered to a subject. Administration route may be selected from intravenous, intraperitoneal, oral, mucosa, skin adsorption, or other available routes. Oral administration is the preferred route. For example, host cells comprising FIP can be immersed in solution and FIP will be absorbed to fish through their gills.

The preferred embodiments of the subject that can be administered with FIP or host cells comprising FIP are mammal, fish, crustacean and poultry. Pig and chicken is the preferred mammal and poultry, respectively. Grouper, salmon and trout are the preferred fish. Shrimp, lobster, *Penaeus monodon, Penaeus japonicus* and *Penaeus vannamei* are the preferred crustacean.

The present invention also relates to a composition for use in modulating immunological activities by oral route comprising fungal immunomodulatory protein. The fungal immunomodulatory protein is prepared from natural Ling Zhi or from the fungal immunomodulatory protein of the process of the invention. According to studies done on the function of the protein of the invention, the said composition could be applied to pharmaceutical use for reducing inflammation and anaphylaxis, modulating immune activity, preventing diabetes, improving asthma, modulating immune responses against bacterial and viral infection, modulating the immune response against organ transplantation; to food or feed additives for prolonging life, modulating immune activity, increasing feed conversion (i.e. the rate of feed weight transferred to body weight) and modulating the negative immune response such as inflammation caused by stress (Black P H, *Brain Behav Immun.* 2003 October; 17(5):350-64.).

The present invention further provides a method of modulating immunological disorders by orally administering FIP to a subject. The protein may be prepared from *E. Coli* or fungi such as *Saccharomyces cerevisiae*.

The invention further provides immunological assays such as western blot or enzyme-linked immunoabsorbant assay (ELISA) to measure the amount of FIP in herbs (such as Ling Zi), foods, beverages, cosmetics, feed addictive, or drugs (*Molecular Cloning: A Laboratory Manual*, 2nd Ed., pp: 18.60-18.75.).

Compositions comprising the protein of the invention may include other agents conventional in the art with regard to the type of formulation. For example, those formulations suitable for oral administration may include other agents such as sweeteners, thickeners and flavoring agents.

The appropriate composites in the compositions comprising the protein of the invention may depend on the type, severity and stage of disease and vary among different individuals.

The following examples are intended to illustrate, but not to limit the invention.

EXAMPLES

Example 1

Preparation of Expression Vectors
pYB101-FIP-yeast and pYB101-FIP-1z

Construction of FIP-yeast and FIP-1z

The DNA sequences of FIP-yeast was depicted in FIG. 1(I) and FIP-1z in FIG. 1(II). The DNA sequences were prepared according to *Proc. Natl. Acad. Sci.* USA. 1991 May 15:88 (10): 4084-4088.

Preparation of Primers of FIP-yeast and FIP-1z

The forward and reverse primers of FIP-yeast and FIP-1z were purchased from commercial suppliers (Mission Biotech Co., Ltd. Taiwan) according to the known DNA sequence encoding Ling Zhi immunomodulatory protein (*J. Biol.*

*Chem.* 1991; 266(4), 2486-2493). Restriction sites of PmlI and BamHI were added to both ends of the primers as depicted in FIGS. 2(I) and 2(II). PCR reaction was performed to obtain the desired primers. The primers amplified were sequenced and their sequences were confirmed.

Construction of Expression Vectors pYB101, pYB101-FIP-yeast and pYB101-FIP-1z

Using techniques currently available, the galactose promoter, gene Ura 3, and 2 ori were introduced to pYB (Yeastern Biotech Co., Ltd., Taiwan) to provide a nutrition selection marker and a yeast replication origin, respectively. The new vector, pYB101, as depicted in FIG. 4 (I), can be transformed to known Baker's yeast such as BY4741 or DY150. The vector pYB101 and DNA sequences encoding FIP-yeast and FIP-1z were digested by restriction enzymes PmlI and BamHI (New England Biolabs, Beverly, USA). The digested fragments were purified using PCR Cleaning Up Purification Kit. (Viogene, Taiwan). Three moles of digested fragments of FIP-yeast or FIP-1z were ligated to one mole of digested pYB 101 by T4 DNA ligase (New England Biolabs, Beverly, USA) to prepare pYB101-FIP-yeast and pYB101-FIP-1z as depicted in FIG. 4 (II) and (III), respectively.

Transformation of pYB101-FIP-yeast and pYB101-FIP-1z into *E. coli*

*E. coli* DH5a were transformed with pYB101-FIP-yeast and pYB101-FIP-1z using standard transformation technique (*Molecular Cloning: A Laboratory Manual*, 2nd Ed. pp: 1.82-1.84). Using commercially available DNA extraction kits (Mini-M Plasmid DNA Extraction Kit, Viogene, Taiwan), large amounts of pYB101-FIP-yeast and pYB101-FIP-1z could be obtained from the transformed *E. coli*.

Example 2

Preparation of Small Amount of FIP-Yeast and FIP-1z Protein

Transformation of pYB101-FIP-Yeast and pYB101-FIP-1z into Baker's Yeast

Baker's yeasts (BY4741 or DY150) were transformed with 1 μg of pYB101-FIP-yeast or pYB101-FIP-1z using yeast transformation kit (Yeastern Biotech Co., Ltd., Taiwan).

Selection of Transformed Yeast By Nutrition Condition

The transformed yeasts said above were spread and cultivated on YNBD media (0.17% Bacto Yeast Nitrogen Base without Amino Acids (Difco, England), 0.5% ammonia sulfate, 2% glucose, 2% agar, (Sigma, USA)). Using the auxotrophic BY4741 (MAT a his3delta1 leu2delta0 met15delta0 ura3delta0) and DY150 (MAT a ura3-52 leu2-3 112 trp1-1 his3-11, 15, ade2-1 can1-100), 0.0024% histidine, 0.0072% leucine, and 0.0012% methionine (BY4741) or 0.0072% leucine, 0.0048% tryptophan, 0.0024% histidine, and 0.0024% adenine (DY150) (Sigma, USA) were added to YNBD media before cultivation. The media was maintained at 30° C. for 2-3 days. Uracil was not supplied in the medium to select the transformed yeast. Both vectors pYB10'-FIP-yeast and pYB101-FIP-1z possess a gene that encodes uracil. Therefore, transformed baker's yeasts will possess such uracil and are able to survive without providing uracil in the medium, whereas non-transformed yeast cannot survive.

Testing Transformed Yeasts in Agitator with Small Volume

The two auxotrophic strains of transformed yeasts said above were inoculated to 50 ml YNBD media added with the required nutrition as described in example 2. The culture was grown at 30° C. and 250 rpm for 3 days. The yeast culture was centrifuged and washed 3 times with YNB culture media to remove glucose. The yeast culture was then adjusted to 0.1 $OD_{600}$ nm in 50 ml of YNBG culture media (0.17% Bacto Yeast Nitrogen Base without amino acids, 0.5% ammonia sulfate, 2% galactose) with the required nutrition. The yeast culture was grown at 30° C. and 250 rpm. The yeast concentration was monitored daily using spectrophotometer Ultrospec 2100 pro (Amersham Pharmacia biotech, USA) to measure the $OD_{600\ nm}$, and 1 ml of yeast sample was harvested everyday. The sample was centrifuged using Microfuge 18 Centrifuge (Bechman Coulter, USA) at 10000×g for 5 minutes and was washed 3 times to obtain the yeast mass. The mass was kept at −20° C.

Example 3

Quantification of Ling Zhi Immunomodulatory Protein Expressed from Transformed Yeast Using Western Blot Analysis The harvested yeast mass were diluted to $OD_{600\ nm}$=0.5 by PBS (Sigma, USA). The diluted mass was dissolved into 2×SDS sample buffer (Sigma, USA) and heated at 100° C. for 3 minutes. After cooling, 10 μl of the diluted mass were subjected to SDS-PAGE at 100 volts following the protocol described in *Nature* (1970) 227, 680-685.

Western blot was performed following the standard protocol in *Molecular Cloning: A Laboratory Manual*, 2nd Ed., pp: 18.60-18.75. The protein on the gel was transferred to the PVDF membrane (Hybond-P, Amersham Bioscience, USA) by 50 mA electrophoresis using Semi-PHOR (Hoefer Scientific Instruments, San Francisco) until all proteins have been transferred. The membrane was then immersed into the blocking buffer at 37° C. for one hour and at 4° C. overnight. After the removal of blocking buffer, $10^{-3}$× rabbit anti-Ling Zhi immunomodulatory protein serum (Taiwan Advance BioPharm Inc., Taiwan) in the blocking buffer were added and incubated with the membrane at 37° C. for one hour. After removing the serum solution and washing the membrane with the washing buffer, $10^{-4}$ HRP-labeled mouse anti-rabbit serum (Sigma, USA) was added to and incubated with the membrane at 37° C. for one hour. After washing the membrane with washing buffer, color indicator TMB (Sigma, USA) was added to develop the color. To complete the western blot assay, the color reaction was terminated when the color appear by adding water. The final result is shown in FIG. 5.

In FIG. 5 (I, II), M and S were standard protein marker and standard FIP purified from *E. coli*. Groups 1-4 were FIP expressed by the improved FIP codon. Groups 2-5 were FIP expressed by the original FIP codon. As shown in FIG. 5 (I), groups 1-3 have FIP clearly expressed, whereas no FIP was detected in groups 5-8. This result shows that the improved FIP codon can be highly expressed in yeast.

Example 4

Preparation of Expression Vectors pYB101s-FIP

Construction of FIP

The template sequence of FIP was depicted the sequence of FIP-yeast depicted in FIG. 1(I). The DNA sequences were prepared as described in Example 3. Yeast BY4741 was selected as the transform host.

Preparation of Primers of FIP

The forward and reverse primers of FIP were purchased from commercial suppliers (Mission Biotech Co., Ltd. Taiwan). PCR reaction was performed using the pYB101-FIP-yeast (FIG. 4) as the template. Restriction sites PmlI and XhoI were added to the primers as depicted in FIGS. 6 (I) and (II). PCR reaction was performed to obtain the desired primers. The DNA amplified was sent to sequence (Mission Biotech Co., Ltd. Taiwan) and their sequences were confirmed.

Construction of Expression Vectors pYB-101s and pYB101s-FIP

Figure 8:
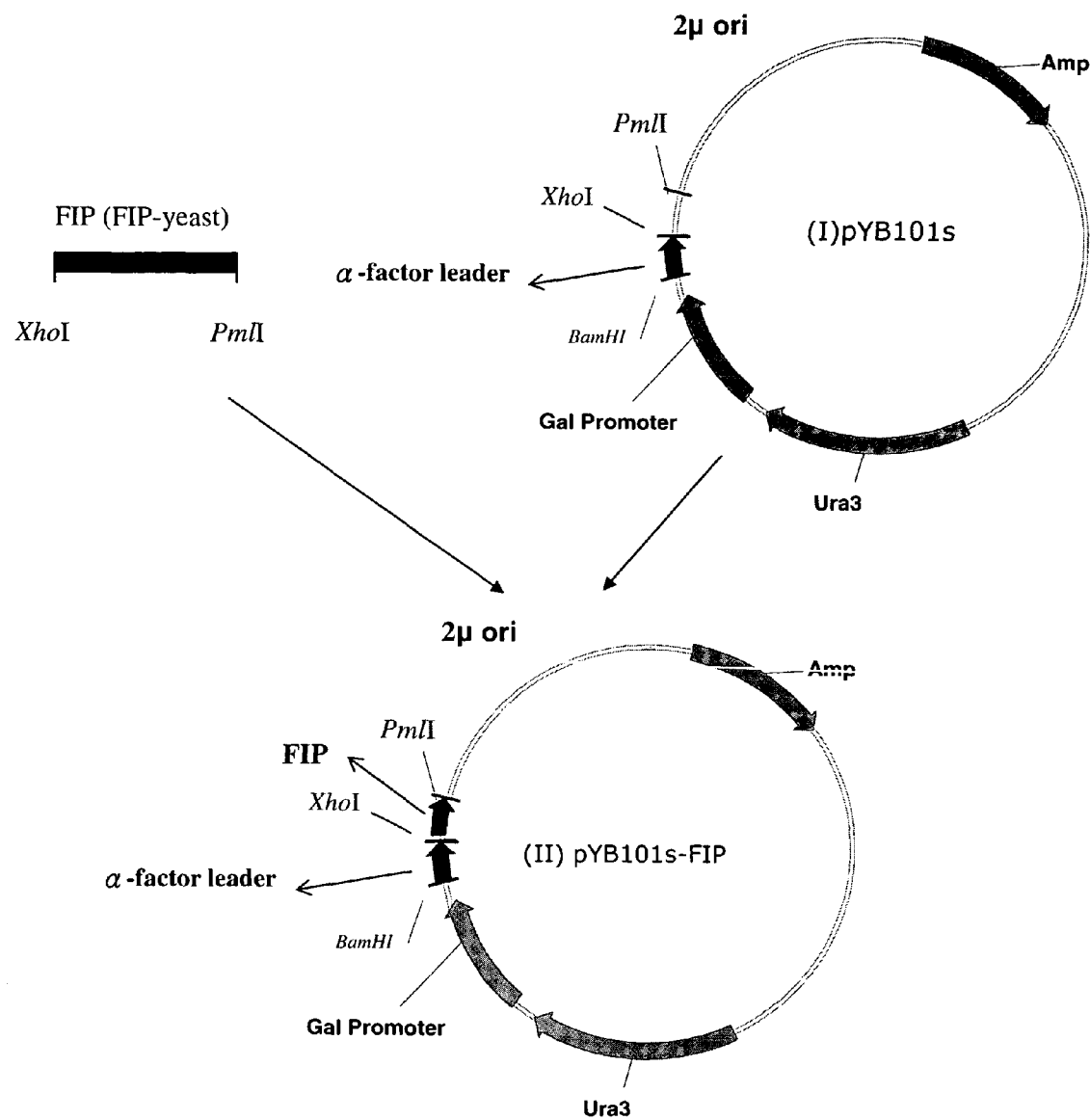
FIG. 8 shows the construct map of plasmid (I) pYB101s (II) pYB101s-FIP.

Using techniques currently available, the galactose promoter, gene Ura 3, 2 ori, and an α-factor leader sequence (as depicted in FIG. 7) were introduced to pYB (Yeastern Biotech Co., Ltd., Taiwan) to provide a nutrition selection marker, a yeast replication origin, and a secretion signal, respectively. The new vector, pYB101s, as depicted in FIG. 8 (I), can be transformed to known Baker's yeast such as BY4741 and their sequences were confirmed by sequencing (Mission Biotech Co., Ltd. Taiwan).

The vector pYB101s and DNA sequences encoding FIP were digested by restriction enzymes PmlI and XhoI (New England Biolabs, Beverly, USA). The digested fragments were purified using PCR Cleaning Up Purification Kit. (Viogene, Taiwan). Three moles of digested fragments of FIP were ligated to one mole of digested pYB101s by T4 DNA ligase (New England Biolabs, Beverly, USA) to prepare pYB101s-FIP as depicted in FIG. 8 (II).

Transformation of pYB101s-FIP into *E. coli*

As described in Example 1, *E. coli* DH5α were transformed with pYB101s-FIP. Large amounts of pYB101s-FIP could be obtained from the transformed *E. coli*.

Example 5

Preparation of Small Amount of FIP

Transformation of pYB101s-FIP into Baker's Yeast BY4741

Baker's yeasts BY4741 were transformed with 1 μg of pYB101s-FIP as described in Example 2.

Selection of Transformed Yeast By Nutrition Condition

The transformed yeasts said above were selected from YNBD agar (w/0.0024% histidine, 0.0072% leucine, 0.0012% methionine) following the same protocol described in Example 2.

Testing Transformed Yeasts in Agitator with Small Volume

The transformed yeasts said above were inoculated to 50 ml YNBD media added with the required nutrition as described in Example 2. The production of FIP protein was induced by adding galactose to the medium, and the secreted FIP was collected everyday.

Example 6

Quantification of FIP Expressed from Transformed Yeast Using SDS-PAGE

Figure 9:
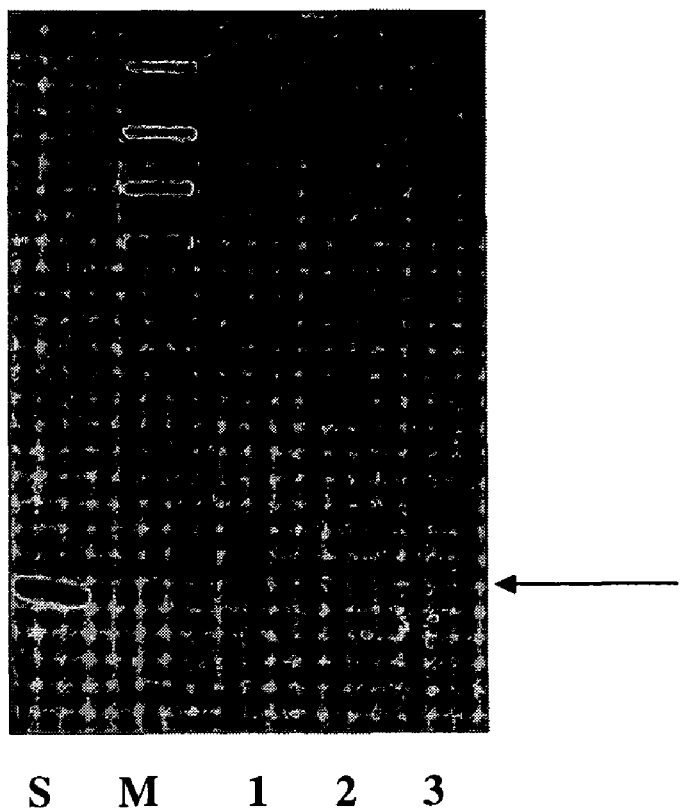
FIG. 9 shows the quantification of FIP expressed by yeast By4741 transformed with pYB101s-FIP. M: Standard protein showing molecular mass 175, 83, 62, 47.5, 32.5, 25, 16.5, and 6.5 Kd. S: The standard FIP prepared from transformed *E. Coli*. Lane 1-3: The first, second and third culture day of By4741 transformed with pYB101s-FIP-yeast.

The sample FIP protein was analyzed by SDS-PAGE as described in Example 3. The gel was then stained with Coomassie brilliant blue G-250 (Sigma) for 30 minutes, and destained with the destain solution (20% methanol, 10% acetic acid) until the protein band is clear. The staining result is shown in FIG. 9.

Example 7

50 L Fermentation Process

Yeast Inoculation in 50 ml Flask.

Transformed yeasts which produces Ling Zhi immunomodulatory protein were selected by western blot analysis and were inoculated to 50 ml YNBD media together with the required nutrition as in Example 2. The culture was maintained at 30° C. and 250 rpm for 24 hours.

Yeast Inoculation in 2000 ml Flask.

The 50 ml culture said was inoculated to the same media 450 ml in a 2000 ml flask. The culture was maintained at 30° C. and 250 rpm for 24 hours.

Yeast Fermentation in 50 L Fermentor (Chuan Tai Factory, Taiwan).

The 500 ml culture said was centrifuged and washed twice with YNB media to remove glucose. The yeast concentration was adjusted to 0.1 $OD_{600\ nm}$ in 50 L YNBG culture media (0.17% Bacto Yeast Nitrogen Base w/o Amino Acids, 0.5% ammonia sulfate, 2% galactose (Sigma, USA)) together with the required nutrition as in Example 2. The yeast culture was fermented three days at 25-30° C., 400-500 rpm, pH 4.5-5.5. The pH value was adjusted by adding required amounts of 2M NaOH and HCl (Sigma, USA). The pressure in the fermentor was maintained at 0.2-0.4 $kg/cm^2$, and 40-50 L/min of ventilation filtrated with 0.2 μm filter.

Quantification of Ling Zhi Immunomodulatory Protein in 50 L Fermentor

Figure 10:
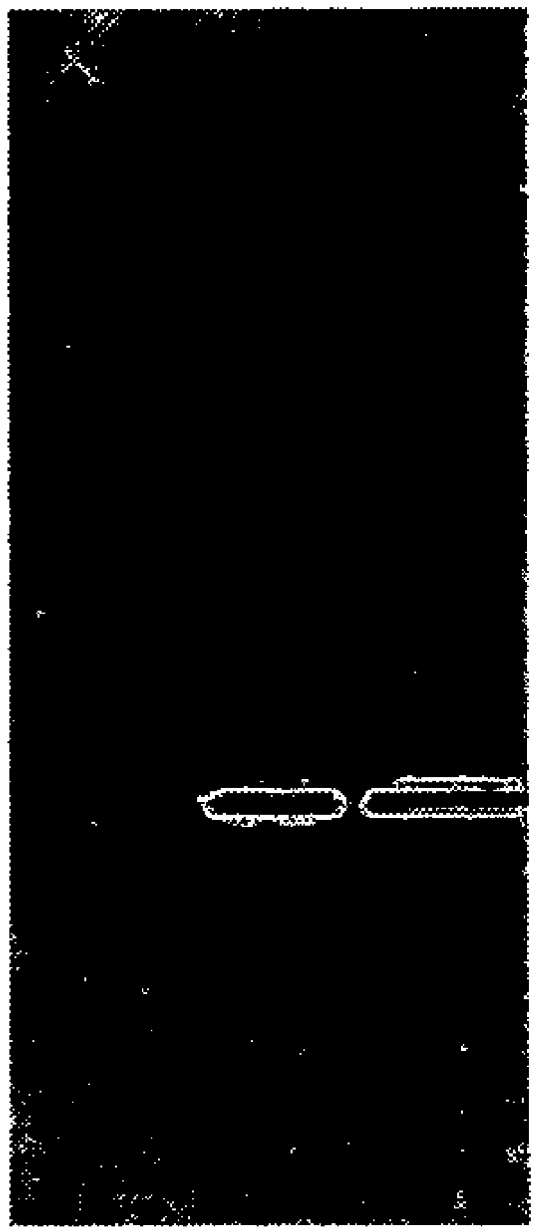
FIG. 10 shows the western blot of samples of 50 L fermentation of yeast comprising FIP. M: Standard proteins. S: Standard FIP generated from *E. Coli*.

As in Example 3, some samples were taken from the fermentation culture and the quantity of Ling Zhi immunomodulatory protein in the sample was determined by western blot analysis. As shown in FIG. 10, the product from 50 L Fermentor has Ling Zhi immunomodulatory protein.

Example 8

Activity Assay of Ling Zhi Immunomodulatory Protein Expressed from Transformed Yeast Preparation of Total Cell Extracts The harvested yeast mass was washed with PBS and centrifuged 3 times. The yeast pellet was collected and 0.4 mm glass beads of the same volume of the pellet were added. Mixture was vortexed for 20 sec at 4° C. and put on ice for 1 min. This step was repeated five times. After centrifuging at 15,000 rpm for 5 min at 4° C., the supernatant was used as a total cell extract.

The sample was centrifuged and supernatant was retained. The supernatant was filtrated by 0.2 μm membrane (Sartorius) and kept for later use.

Preparation of Human Peripheral Mononuclear Cells (PMNC)

Heparinized peripheral bloods were collected from adults and Ficoll-paque culturing media (Amersham Biosciences) was added the blood sample. Following the Amersham protocol, the solution was centrifuged to separate PMNC. Cells were plated at the concentration of $1 \times 10^6$ cells/ml in 24-well plate (Nunc, Roskilde, Denmark) for tissue culture. Each 1 ml culture media contains 10% FBS 100 μg/ml streptomycin 100 units/ml penicillin and 200 mM L-glutamate of RPMI1640 medium (GIBCO, Grand Island, N.Y.). Cells were cultivated after growing at 37° C. for 0, 24 or 48 hours.

Figure 11:
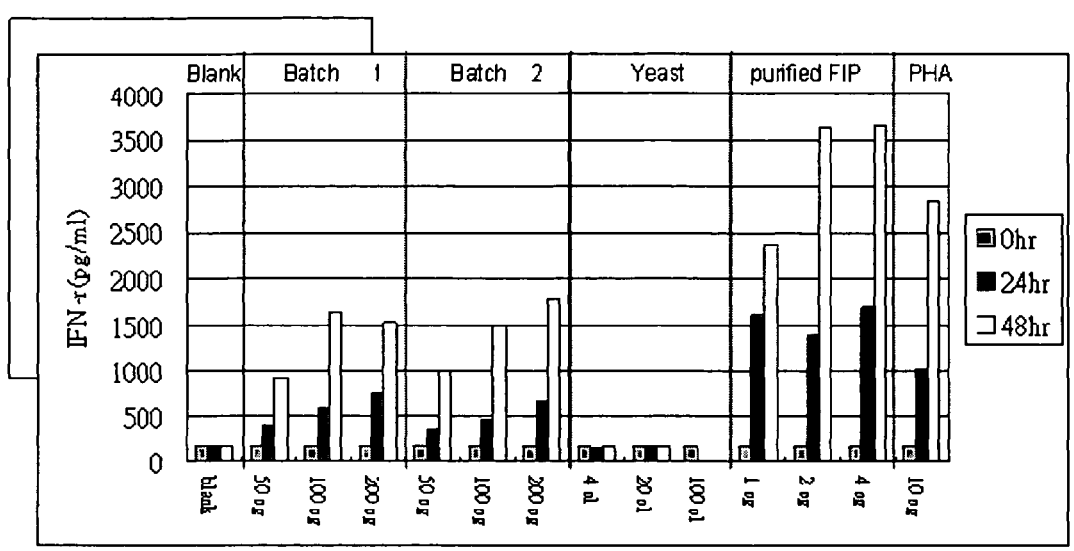
FIG. 11 shows the amount of INF-γ generated by peripheral blood cell (PBL) incubated with different concentrations of FIP prepared by different procedures. Blank: PBS control. Batch 1: Supernatant ruptured yeasts prepared from the first 50 L fermentation process. Batch 2: Supernatant of ruptured yeasts prepared from the second 50 L fermentation process. Yeast: Supernatant of ruptured yeast purchased from the market. PHA: phytohemagglutinin.

Cytokine Assay:

Cells were plated at the concentration of $1 \times 10^6$ cells/ml in 24-well plate (Nunc, Roskilde, Denmark) with different concentrations of Ling Zhi immunomodulatory protein added. Cells were cultivated and INF-γ activity was assayed using commercial kit (R&D Systems, Minneapolis, Minn.). Results are shown in FIG. 11. In FIG. 11, Batch 1 and Batch 2 were samples added with different concentrations of FIP. PHA (phytohaemagglutinin, sigma) was used to test INF-γ activity using standard ELISA technique. (*The Journal of Immunology*, 1998, 161: 2114-2119). The blank and yeast groups clearly showed few INF-γ activity, whereas batches 1 and 2, which have purified FIP and PHA added to cells, showed significant INF-γ activity. The results showed that adding 4 μg purified FIP to PMNC grown for 48 hours can induce more IFN-γ than adding other proteins. The result also showed samples from 50 L fermentation process produce increased amount of IFN-γ, indicating the activity of FIP is not a result of the yeast.

Example 9

Purification of FIP

The fermented yeasts were dissolved 1:10 (v/v) in 20 mM PBS (Sigma), pH 6.0. Cells were disrupted by disrupter (Basic Z model (Constant System Ltd. UK)) under 30 Kpsi. The pH of the solution was modified to pH 4-5 by adding 1M acetic acid. The solution was centrifuged at 3000 g for 15 minutes. The supernatant was separated and centrifuged again at 12,000 g for 1 minute. 10 mL of the supernatant was added to 30 mL of CM Sepharose column (Amersham Biosciences), which was equilibrated with 20-50 mM acetic acid to maintain pH 4-5. Adding 20-50 mM acetic acid solution, pH 4-5, eluted Ling Zhi immunomodulatory protein.

From FIG. 12 (I), F3, F4 and F5 represents samples from the $3^{rd}$, $4^{th}$ and $5^{th}$ collection tubes. F3 and F4 clearly had higher mAU value. F3 and F4 were further analyzed by SDS-PAGE as shown in FIG. 12 (II). In FIG. 12 (II), F3, F4 and F5 were the 3rd, 4th and 5th collecting tubes. STD represents the standard sample (the purified FIP produced from *E. coli*). M was the standard molecular weight. Proteins in F3 and F4 showed the same molecular weight as the STD. The protein bands in F3 and F4 were further confirmed to be FIP by western blot. This result showed that FIP in F3 and F4 is of very high purity.

Example 10

The Application of Ling Zhi Protein

Application of Ling Zhi Protein as Feed Additive.
Toxicity Test of Ling Zhi Protein
Groupers with an average weight 5.9 g and average length 7.25 cm were collected at 25° C. and 33 ppt salty degree. FIP purified as in example 9 was intraperitonelly administered to juvenile groupers at the concentrations 5, 1, 0.25 μg/fish/0.1 ml. PBS solution was administered to the control group. These fish were grown in the original flowing water for 14 days. Fish mortalities were recorded daily. No death was observed in the first two weeks. Therefore, FIP at the above concentrations did not show any toxicity in groupers.

Enhancement of Nonspecific Immune Response by FIP
In Vitro Enhancement of Nonspecific Immune Response by Treating Grouper's Head-Kidney Cells With FIP
Six hundred grams groupers were purchased from the market. Head-kidney cells were cultured and phagocytes were separated using standard culture techniques. Head-kidney cells are the main cells affecting nonspecific immune response in groupers (Engelsma MY, *Fish Shellfish Immunol.* 2003 November; 15(5):397-410). These cells were suspended in AL-10 culturing solution (L15(Gibco):AIM5 (Gibco)=1:1) and 0.1 ml was inoculated at the concentration of $10^7$/ml in 96-well plates (Corning). The plates were maintained at 25° C. for 2 hours.

FIP at concentrations 2, 1, 0.5, 0.2 and 0.02 μg/0.1 ml were added to the head-kidney culture at room temperature for 2 hours. Nitroblue tetrazolium assay (NBT assay, Sigma) was performed to measure the non-specific immune response. The higher the $A_{620\ nm}$ value, the higher enhancement of non-specific phagocytosis.

Figure 13:
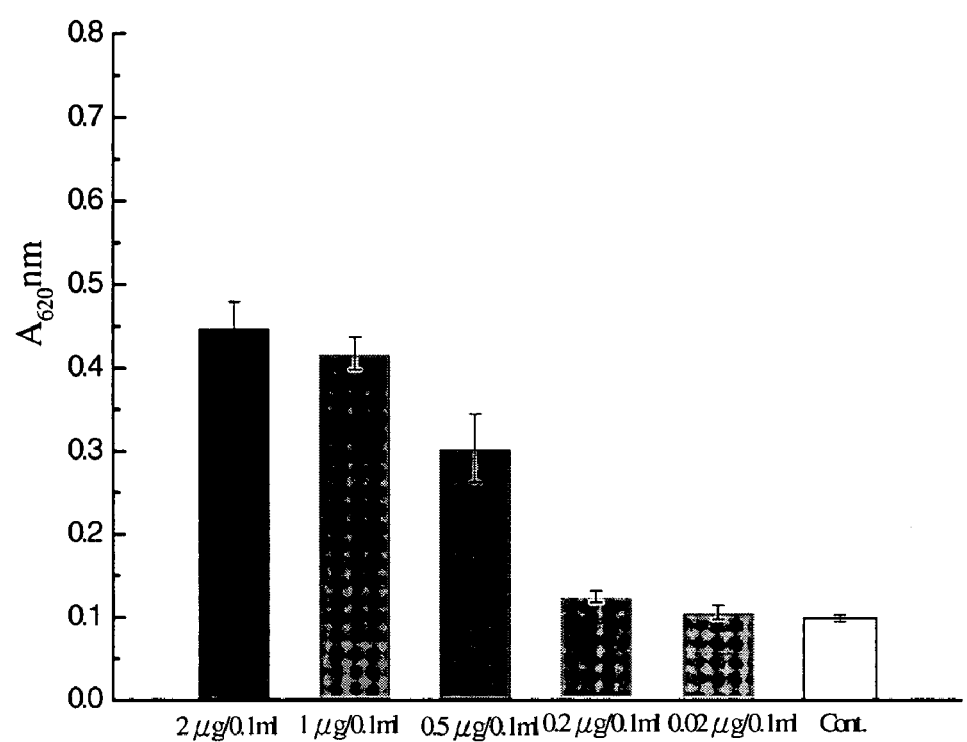
FIG. 13 shows the result of NBT assay on grouper's head-kidney cells under different concentrations of purified FIP. Control: PBS control.

Adding FIP to the head-kidney cells enhances phagocytosis, which was measured by the NBT assay. As shown in FIG. 13, adding 2, 1 and 0.5 μg/0.1 ml FIP clearly increased the phagocytosis of head-kidney cells, suggesting that FIP can enhance nonspecific immunological response.

Figure 14:
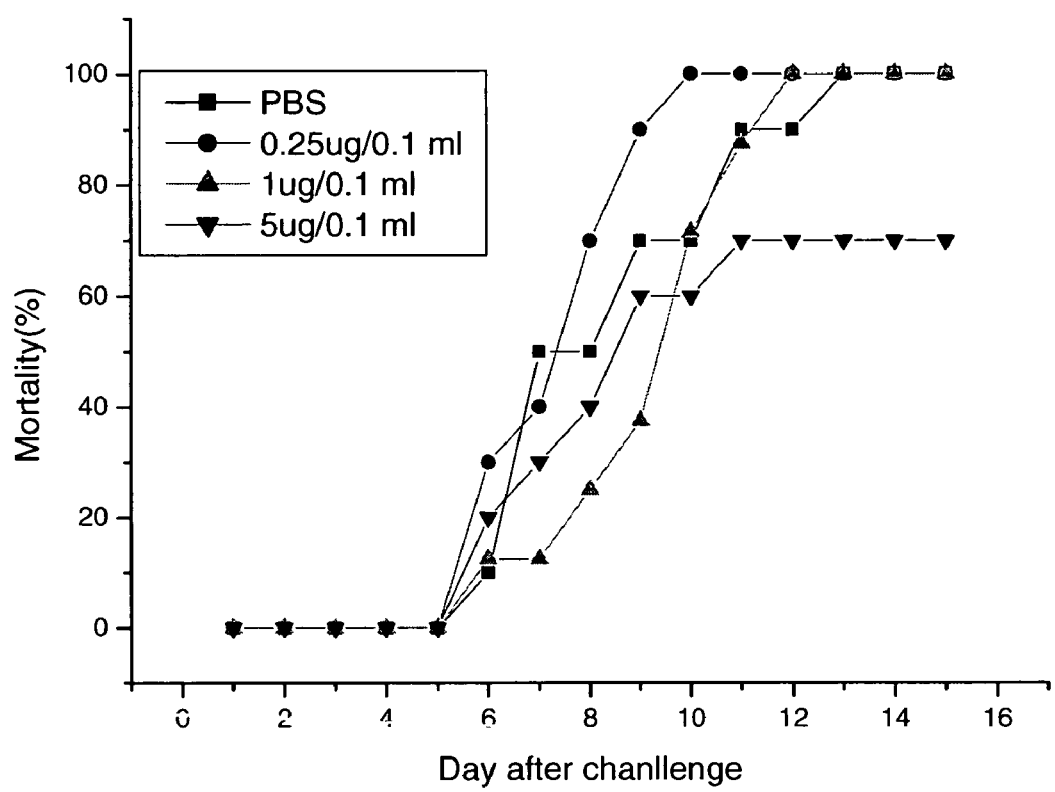
FIG. 14 shows the mortalities of groupers challenged with Iridovirus infection after injecting different concentrations of FIP to their abdomen. PBS: Intraperitoneal injecting 0.1 ml PBS before virus challenging. 0.25, 1, 5 ug/0.1 ml: Intraperitoneal injecting 0.25, 1, 5 ug/0.1 ml purified FIP before virus challenging.

Fish Protection of FIP Against Iridovirus
Groupers were administered with PBS or FIP intraperitoneally as said in the previous experiment. After growing for three weeks, 0.1 ml of 10,000×$TCID_{50}$ viral dosage was administered to the peritoneum of these fish. Fish mortalities were recorded daily. In general, groupers administered intraperitoneally with Iridovirus died in 2 weeks. As shown in FIG. 14, fish administered with the highest dosage of FIP, 5 μg FIP/fish/0.11 ml, showed 70% mortality after two weeks. Therefore, 30% protective rate was achieved in two weeks.

Fish Protection Against *Vibrio harveyi* Infection.
One hundred groupers (*Epinephelus malabevicus*, average weight 52.9 g) were separated into five groups. Each group included 20 groupers:
1. PBS control;
2. Groupers fed with 20 mg original yeast/60 g body weight;
3. Groupers fed with 20 mg FIP-comprising yeast/60 g body weight;
4. Groupers fed with 4 mg FIP-comprising yeast/60 g body weight;
5. Groupers fed with 0.8 mg of FIP-comprising yeast/60 g body weight;

Each group was fed once every two days. After 7 days each group were challenged by *Vibrio harvey* infection.

Groupers were challenged with *Vibrio harvey* at ten times the semi-lethal dosage ($LD_{50}$) $3\times10^6$ CFU/ml. Blood samples from 10 fish of each group were collected before the challenge. Nonspecific immunological reactions including lysozyme activity were tested using blood samples said. The other ten fish of each group were challenged with *Vibrio harvey*. The viability, diet and mortality of the fish were recorded daily.

Figure 15:
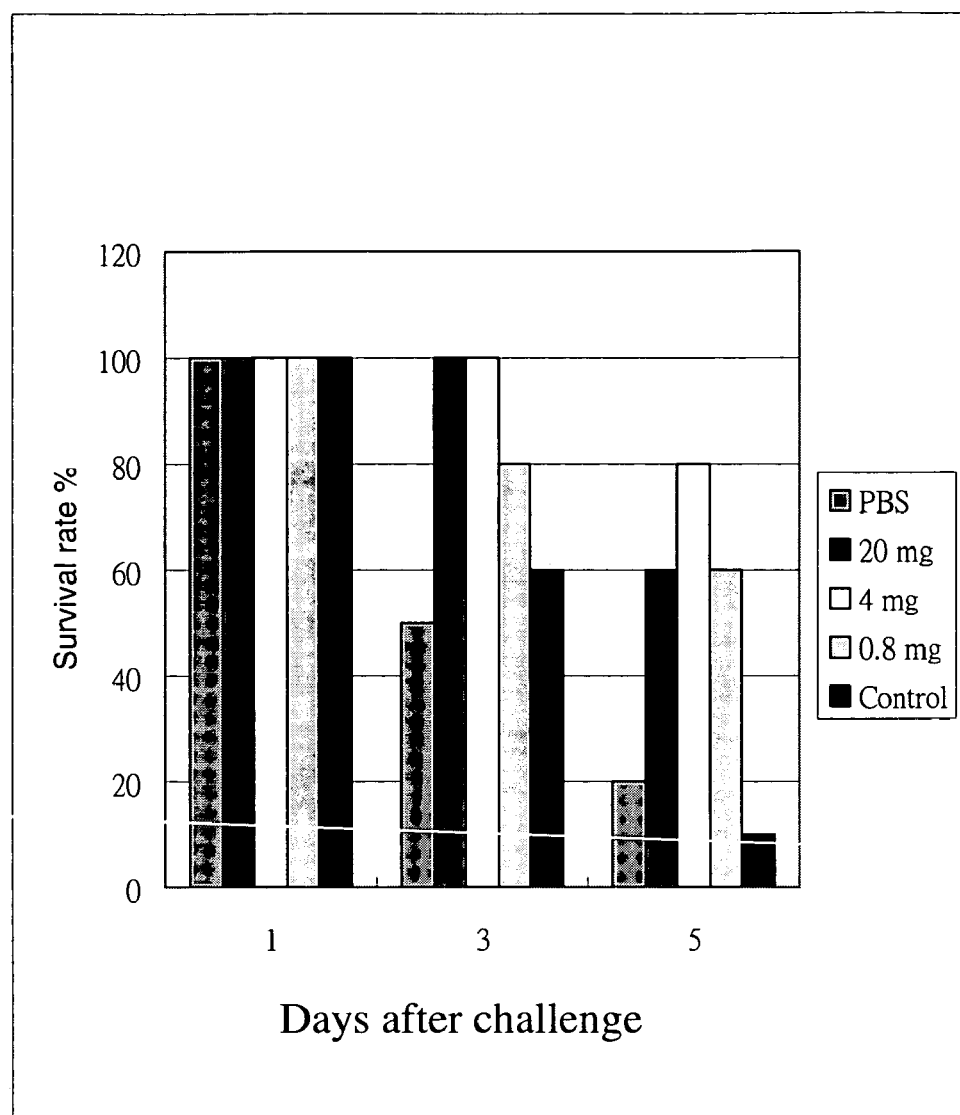
FIG. 15 shows the survival rate of groupers challenged with *Vibrio harveyi* infection after groupers were fed with different amounts of yeast comprising FIP. PBS: Phosphate buffer control. 20 mg, 4 mg, 0.8 mg: Groupers fed with 20 mg, 4 mg, and 0.8 mg yeast comprising FIP. Control: Groupers fed with non-transformed yeast.

As shown in FIG. 15, after being challenged by *Vibrio Harvey* infection, the 5th-day survival rate of PBS and original yeast groups were significantly reduced to 10-20%; however, the survival rate of three FIP-comprising yeast groups were within 60-80%, suggesting that oral administration of FIP is sufficient to enhance fish immunity and lengthen fish life.

Example 11

Measured IFN-γ in Der p-sensitized Splenocytes from Balb/c Mice Re-stimulated with FIP or Der p Extract FIP or Der p Stimulation
Spleen cells were collected from two groups of Der p (House dust mite *Dermatophagoides* antigen (Der pII))-sensitized Balb/c mice. Mice of the FIP groups were fed with 2 μg of FIP every two days. Mice of the Der p groups were administered IP with Der P on the first and $7^{th}$ day and sprayed with Der p on the $14^{th}$ day. Mice were sacrificed on the $15^{th}$ day and spleen cells were collected.

Splenocytes isolated form mice were cultured in 5% RPMI-1640 medium at $6\times10^6$ cells/ml. Splenocytes were then re-stimulated with 10 μg/ml Der p II or 2 μg/ml FIP. Splenocytes in the control group were added with PBS. Culture supernatants were harvested after 48 hours and the amount of IFN-γ produced was analyzed.

Figure 16:
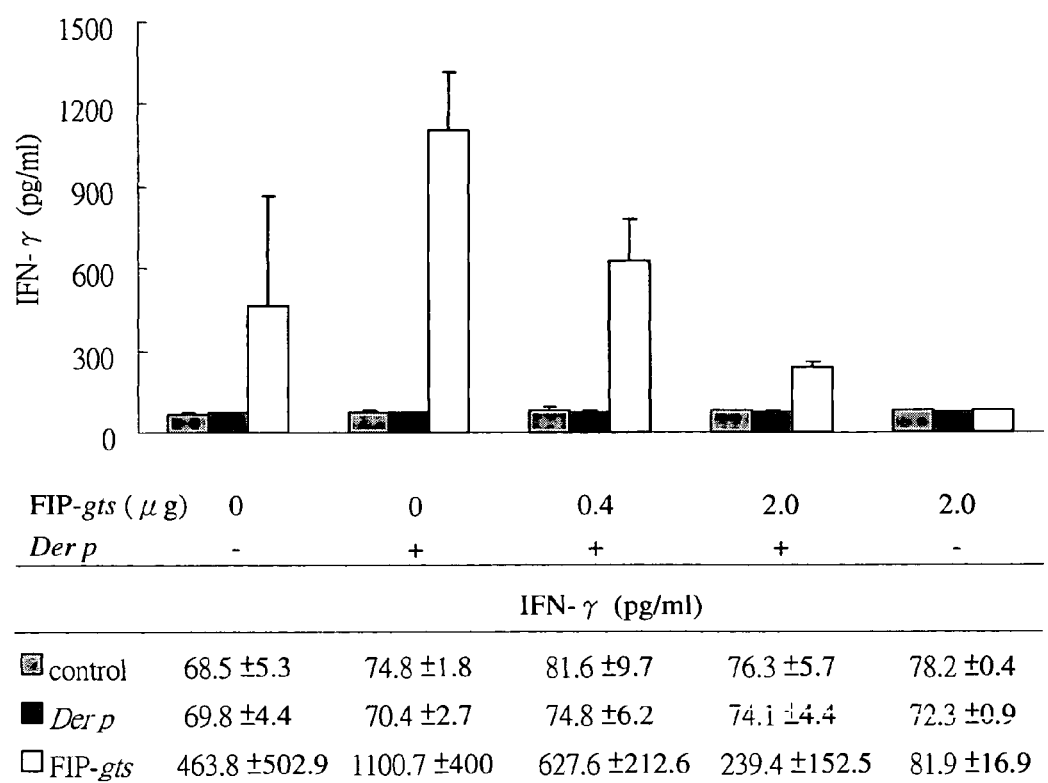
FIG. 16 depicts the IFN-γ expression of splenocytes of Der p II-sensitized Balb/c mice re-stimulated with FIP or Der p II Extract. FIP-gts: FIP. Der p: House dust mite *Dermatophagoides* antigen (Der p2). Control: PBS control.

In FIG. 16, Der p denoted Der p II. FIP-gts denotes FIP. There was no difference of the amount of IFN-r produced between splenocytes from Balb/c mice in the control group and splenocytes from Balb/c mice fed with FIP (81.8 pg/ml). Further, splenocytes from Balb/c mice not fed with FIP or from Der p-stimulated mice will produce more IFN-r (463.8 and 1100.7) than the control if re-stimulated with FIP. This experiment demonstrated that FIP could function via oral administration and modulates immunological activity, especially directly inhibiting anaphylactic.

While the invention has been described and exemplified in sufficient details for those skilled in the art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The plasmids, cell lines, uses, processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be, within, the scope of this invention as defined by the appended claims.

The invention claimed is:

1. A method of modulating immunological activities consisting of:
   (a) transforming yeast cells with a nucleic acid molecule comprising SEQ ID NO. 1;
   (b) expressing a recombinant protein; and
   (c) orally administering the recombinant protein isolated from the yeast cells or the yeast cell expressing the recombinant protein.

2. The method according to claim 1, wherein the yeast cells are *Saccharomyces cerevisiae*.

* * * * *